US010335259B2

(12) United States Patent
Frid

(10) Patent No.: US 10,335,259 B2
(45) Date of Patent: Jul. 2, 2019

(54) 3D FILTER FOR PREVENTION OF STROKE

(71) Applicant: FRID MIND TECHNOLOGIES, Beersel (BE)

(72) Inventor: Noureddine Frid, Beersel (BE)

(73) Assignee: FRID MIND TECHNOLOGIES, Beersel (BE)

( * ) Notice: Subject to any disclaimer, the term of this patent is extended or adjusted under 35 U.S.C. 154(b) by 250 days.

(21) Appl. No.: 15/505,451

(22) PCT Filed: Aug. 21, 2015

(86) PCT No.: PCT/EP2015/069219
§ 371 (c)(1),
(2) Date: Feb. 21, 2017

(87) PCT Pub. No.: WO2016/026953
PCT Pub. Date: Feb. 25, 2016

(65) Prior Publication Data
US 2017/0239033 A1  Aug. 24, 2017

(30) Foreign Application Priority Data

Aug. 21, 2014 (EP) ..................................... 14181860

(51) Int. Cl.
*A61F 2/01* (2006.01)
*A61L 31/02* (2006.01)
(Continued)

(52) U.S. Cl.
CPC .................. *A61F 2/01* (2013.01); *A61F 2/90* (2013.01); *A61L 31/022* (2013.01); *A61L 31/08* (2013.01);
(Continued)

(58) Field of Classification Search
CPC .... A61F 2/01; A61F 2/013; A61F 2/04; A61F 2/06; A61F 2/82; A61F 2/86; A61F 2/90;
(Continued)

(56) References Cited

U.S. PATENT DOCUMENTS 5,061,275 A   10/1991  Wallsten et al.
6,673,089 B1   1/2004  Yassour et al.
(Continued)

FOREIGN PATENT DOCUMENTS

EP          1248372 A2   10/2002
WO       2013082555 A1    6/2013
WO       2013132478 A2    9/2013

OTHER PUBLICATIONS

International Search Report dated Oct. 21, 2015 for International Application No. PCT/EP2015/069219 filed Aug. 21, 2015.
(Continued)

*Primary Examiner* — Ryan J. Severson
(74) *Attorney, Agent, or Firm* — Avery N. Goldstein; Blue Filament Law PLLC

(57) ABSTRACT

The present invention relates to implantable endoluminal prosthesis for preventing stroke. The endoluminal prosthesis (1) consists of a braided framework (20) defining a cylindrical lumen (21) devoid of impermeable membrane. Said braided framework (20) is self-expandable comprising a plurality of layers (22, 23, 24) of wires (25) made of biocompatible material. Each layer forms a mesh. The meshes form a lattice with a plurality of wires (2) of given layers (22, 23, 24). The lattice defines polygonal opening units (26) when observed normal to a wall of the implantable endoluminal prosthesis (1). The diameter ($\varnothing_{25}$) of wire (25) being at least 30 μm and at most 150 μm, the mean diameter ($\varnothing_{27}$) of the inscribed circle (27) of the polygonal opening units (26) being at least 75 μm and at most 200 μm in fully expanded state. The braided framework (20) consists of at
(Continued)

least 128 and at most 512 wires (25). The ratio ($T_1/\varnothing_{25}$) of the thickness ($T_1$) of a wall of said implantable endoluminal prosthesis (1) to the diameter ($\varnothing_{25}$) of wire (25) is at least 3.0. In a fully expanded state, the surface coverage ratio (SCR) of said braided framework (20) is more than 50% and less than 90%.

15 Claims, 14 Drawing Sheets

(51) Int. Cl.
*A61L 31/08* (2006.01)
*A61F 2/90* (2013.01)
*A61L 31/14* (2006.01)
*A61F 2/966* (2013.01)

(52) U.S. Cl.
CPC .............. *A61L 31/088* (2013.01); *A61L 31/14* (2013.01); *A61F 2/966* (2013.01); *A61F 2002/016* (2013.01); *A61F 2210/0076* (2013.01); *A61F 2230/0006* (2013.01); *A61F 2230/008* (2013.01); *A61F 2230/0069* (2013.01); *A61L 2400/18* (2013.01)

(58) Field of Classification Search
CPC .......... A61F 2002/016; A61F 2002/018; A61F 2002/068; A61F 2210/0014; A61F 2210/0076; A61F 2230/0006; A61F 2230/0069
See application file for complete search history.

(56) References Cited

U.S. PATENT DOCUMENTS

| | | | | |
|---|---|---|---|---|
| 6,740,112 | B2 | 5/2004 | Yodfat et al. | |
| 7,588,597 | B2* | 9/2009 | Frid | A61F 2/90 623/1.15 |
| 8,192,484 | B2* | 6/2012 | Frid | A61F 2/856 623/1.15 |
| 8,715,338 | B2* | 5/2014 | Frid | A61B 17/12022 606/200 |
| 2003/0100940 | A1 | 5/2003 | Yodfat | |
| 2004/0215332 | A1* | 10/2004 | Frid | A61F 2/90 623/1.22 |
| 2006/0015138 | A1 | 1/2006 | Gertner | |
| 2007/0162104 | A1 | 7/2007 | Frid | |
| 2011/0046719 | A1* | 2/2011 | Frid | A61B 17/12022 623/1.18 |
| 2014/0303667 | A1* | 10/2014 | Cox | A61F 2/01 606/200 |
| 2015/0039016 | A1* | 2/2015 | Naor | A61F 2/01 606/200 |
| 2017/0239033 | A1* | 8/2017 | Frid | A61F 2/01 |
| 2018/0064525 | A1* | 3/2018 | Frid | A61F 2/2418 |
| 2018/0228590 | A1* | 8/2018 | Frid | A61F 2/01 |

OTHER PUBLICATIONS

Order et al., "Comparison of 4 Cerebral Protection Filters for Carotid Angioplasty: An in Vitro Experiment Focusing on Carotid Anatomy", J. Endovasc. Ther., Apr. 2004, vol. 11, issue 2, pp. 211-218, Copyright The International Society of Endovascular Specialists (2004).
Ou et al., "Aortic arch shape deformation after coarctation surgery: Effect on blood pressure response", J. Thorac. Cardiovasc. Surg., Nov. 2006, vol. 132, issue 5, pp. 1105-1111, Copyright The American Association for Thoracic Surgery (2006).
Oake et al., "Frequency of adverse events in patients with poor anticoagulation: a meta-analysis", Canadian Medica Association Journal, May 22, 2007, vol. 176, issue 11, pp. 1589-1594, Copyright Canadian Medical Association (2007).
Charalambous et al., "Reduction of cerebral embolization in carotid angioplasty: an in-vitro experiment comparing 2 cerebral protection devices", J. Endovasc. Ther., Apr. 2009, vol. 16, issue 2, pp. 161-167, Copyright The International Society of Endovascular Specialists (2009).
Sievert et al., "A Novel Carotid Device for Embolic Diversion: Lessons Learned from a "First in Man" Trial in Patients with Atrial Fibrillation", CardiovasC. Intervent. Radiol., Apr. 2012, vol. 35, issue 2, pp. 406-412, Copyright Springer Science+Business Media, LLC and the Cardiovascular and Interventional Radiological Society of Europe (CIRSE) (2011).

* cited by examiner

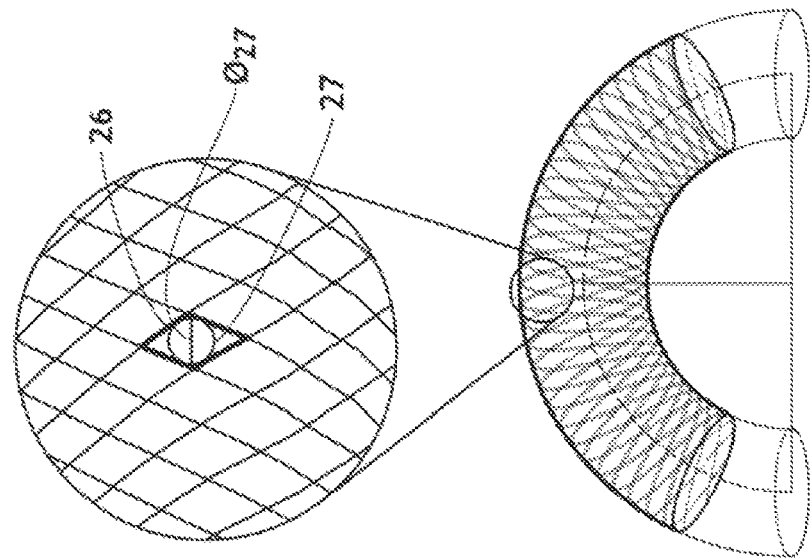
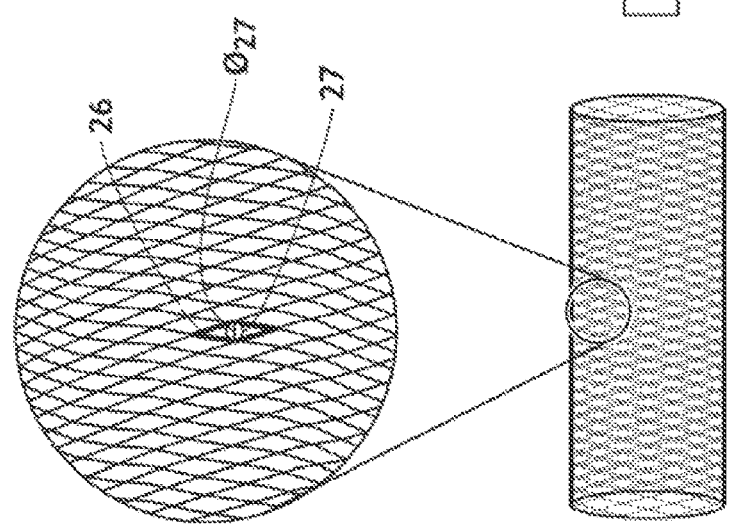
Fig. 1a (Prior Art)
Fig. 1b (Prior Art)

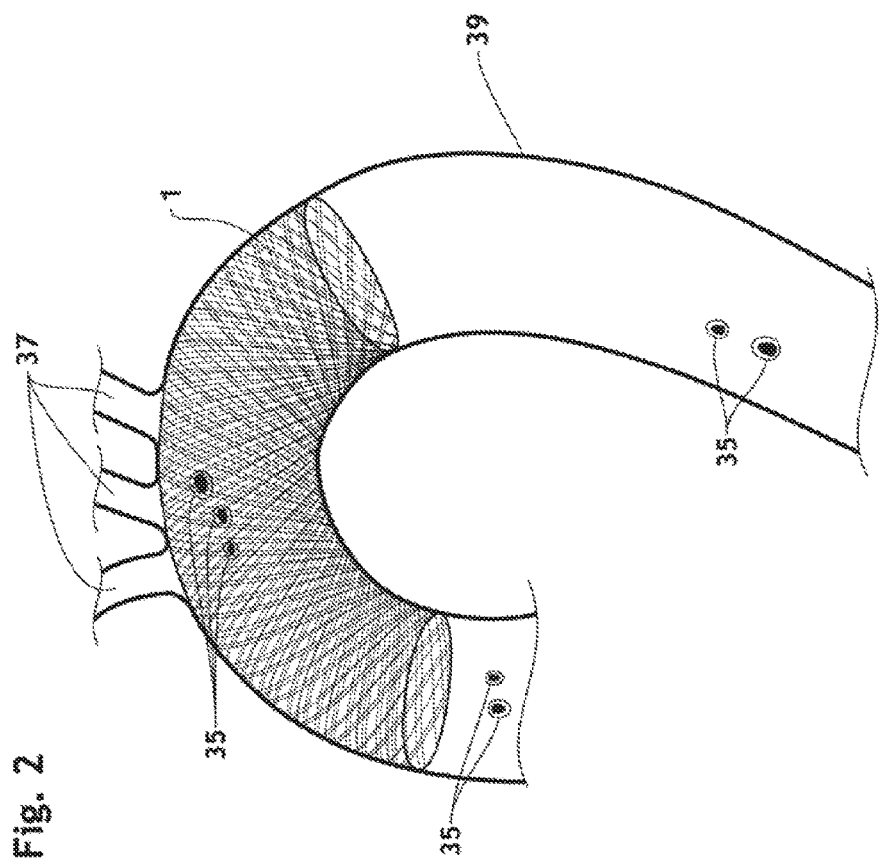

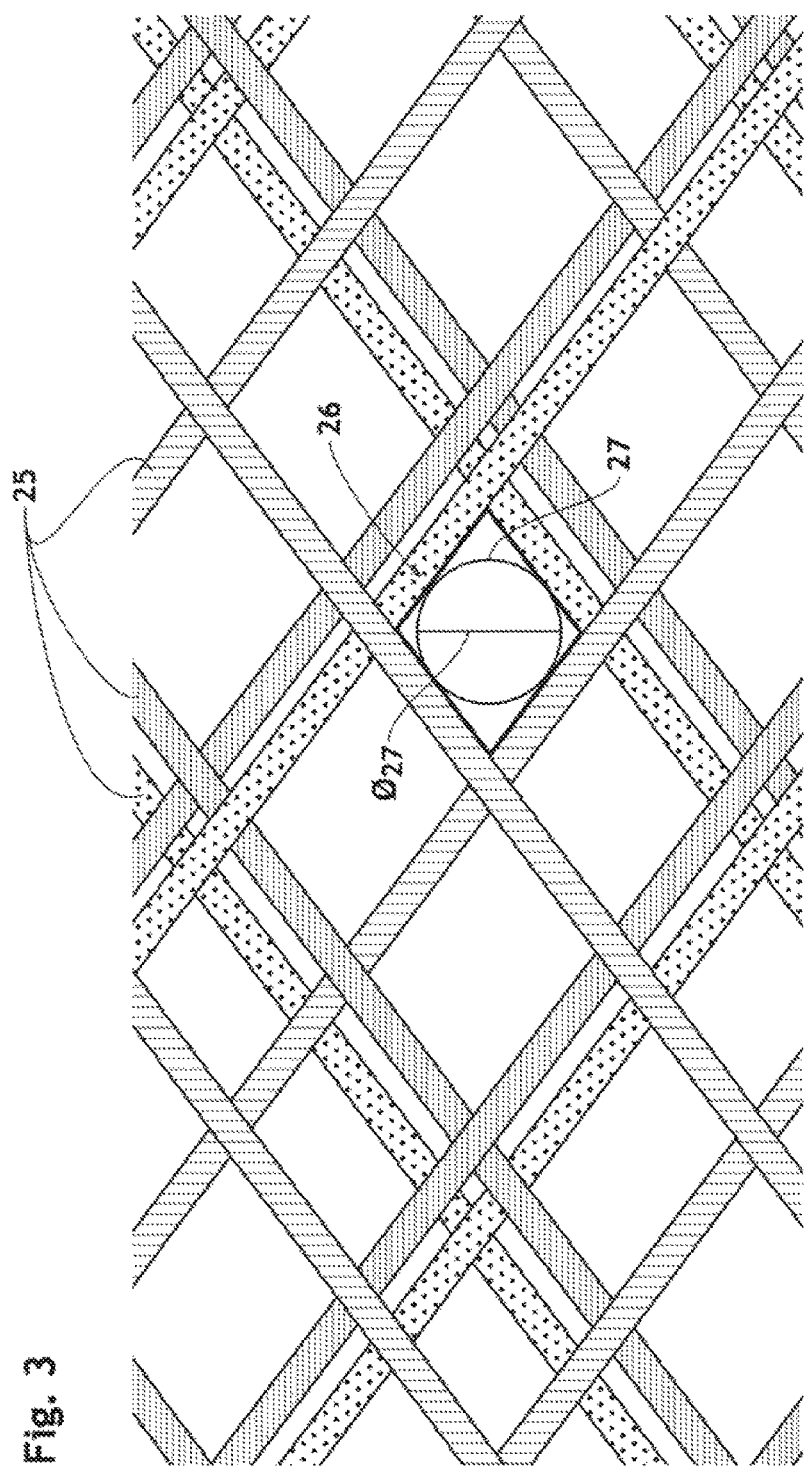

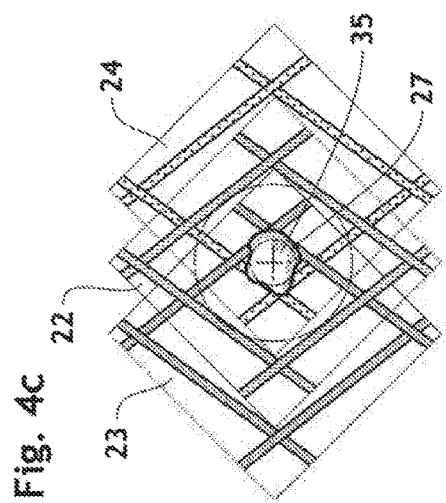
Fig. 4a  Fig. 4b  Fig. 4c
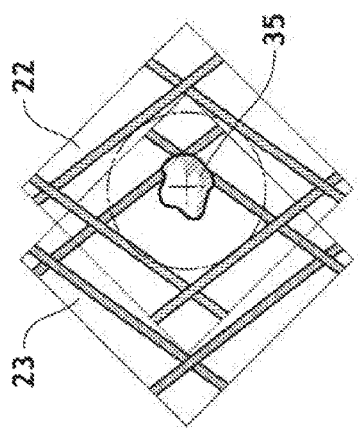
Fig. 5a  Fig. 5b  Fig. 5c
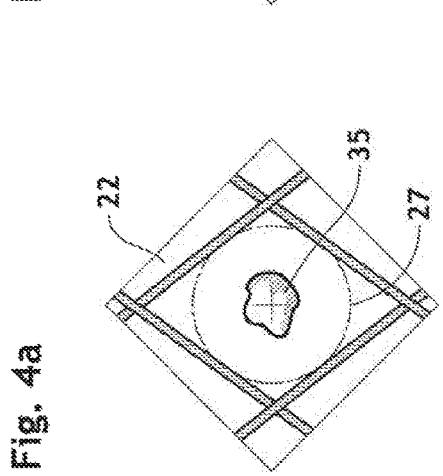
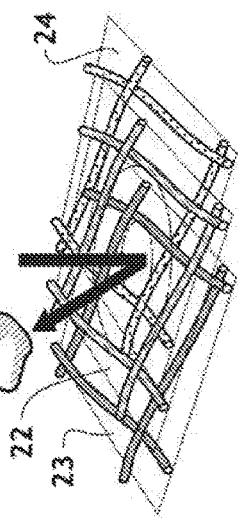
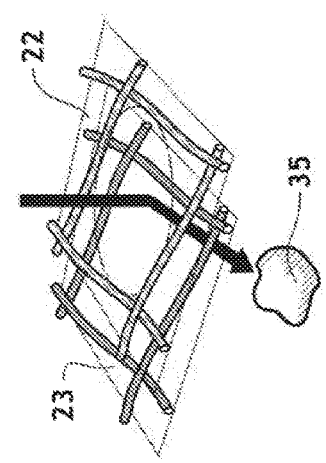
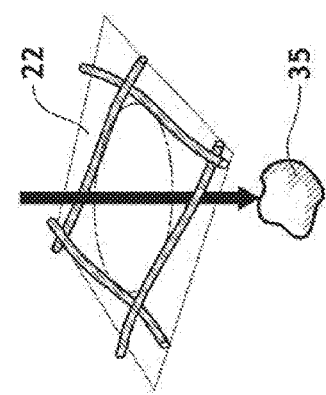

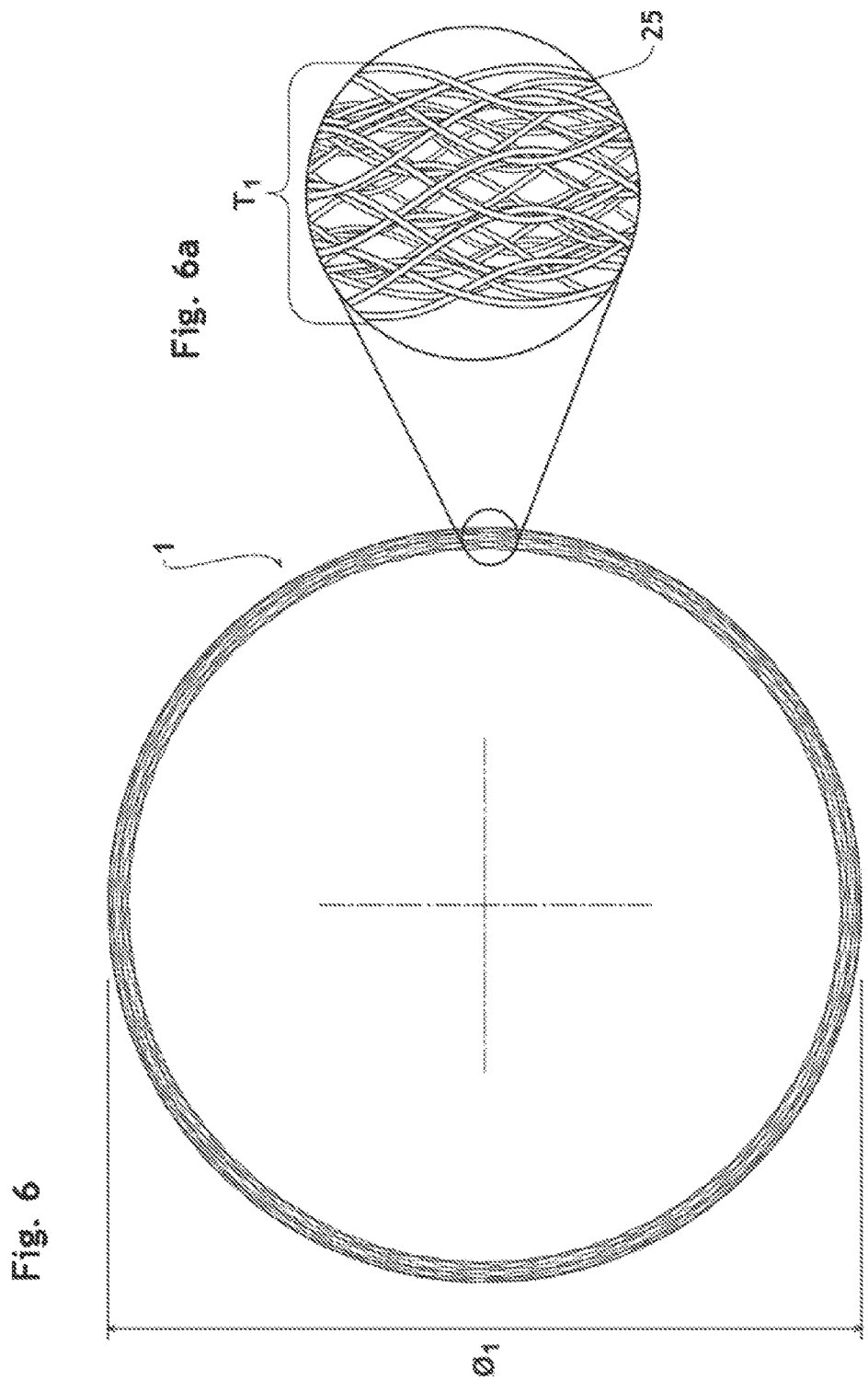

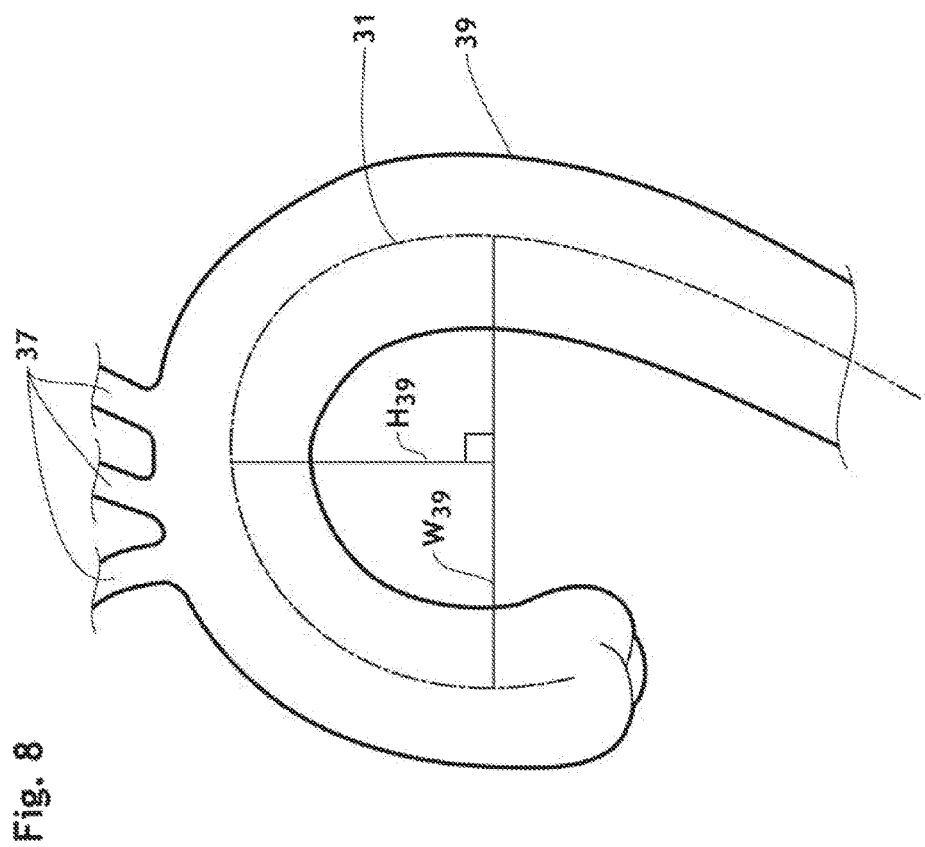

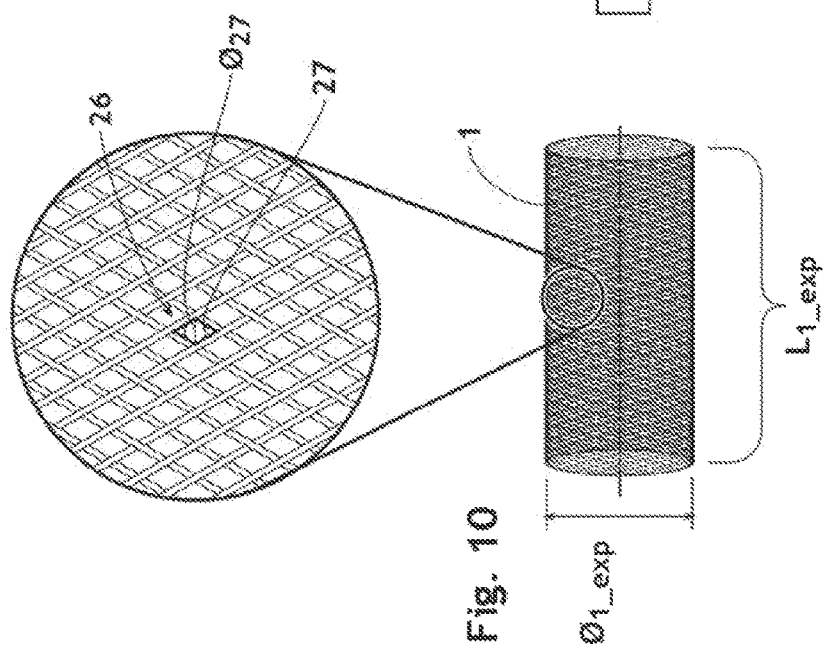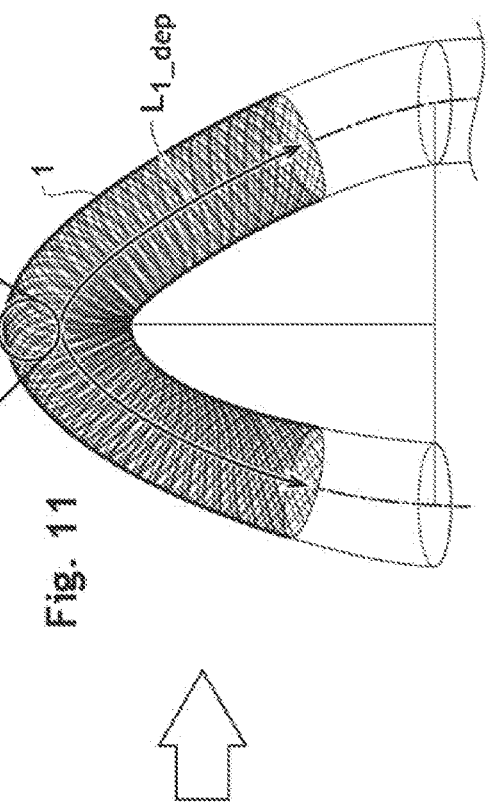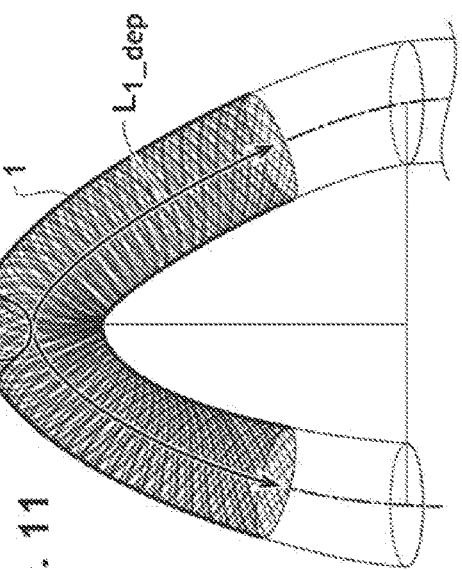

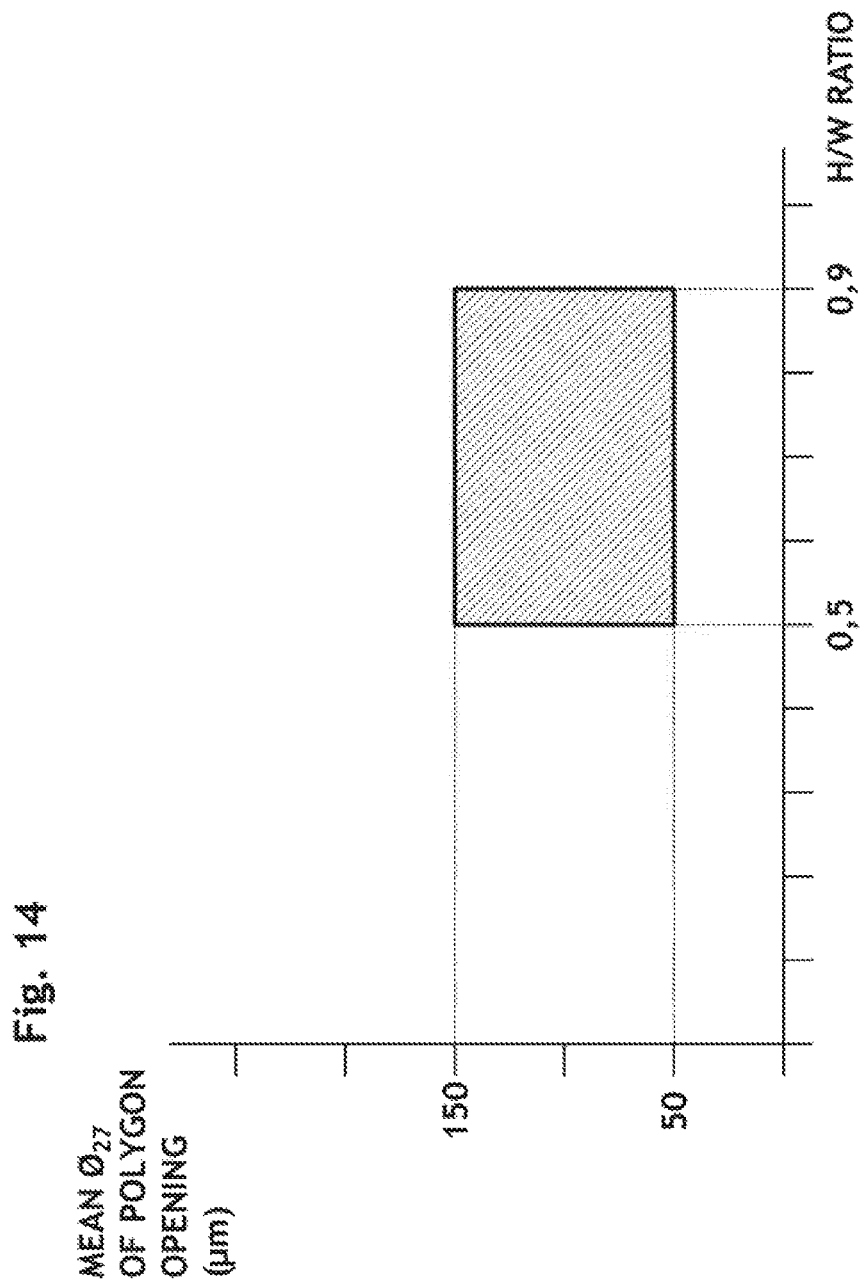

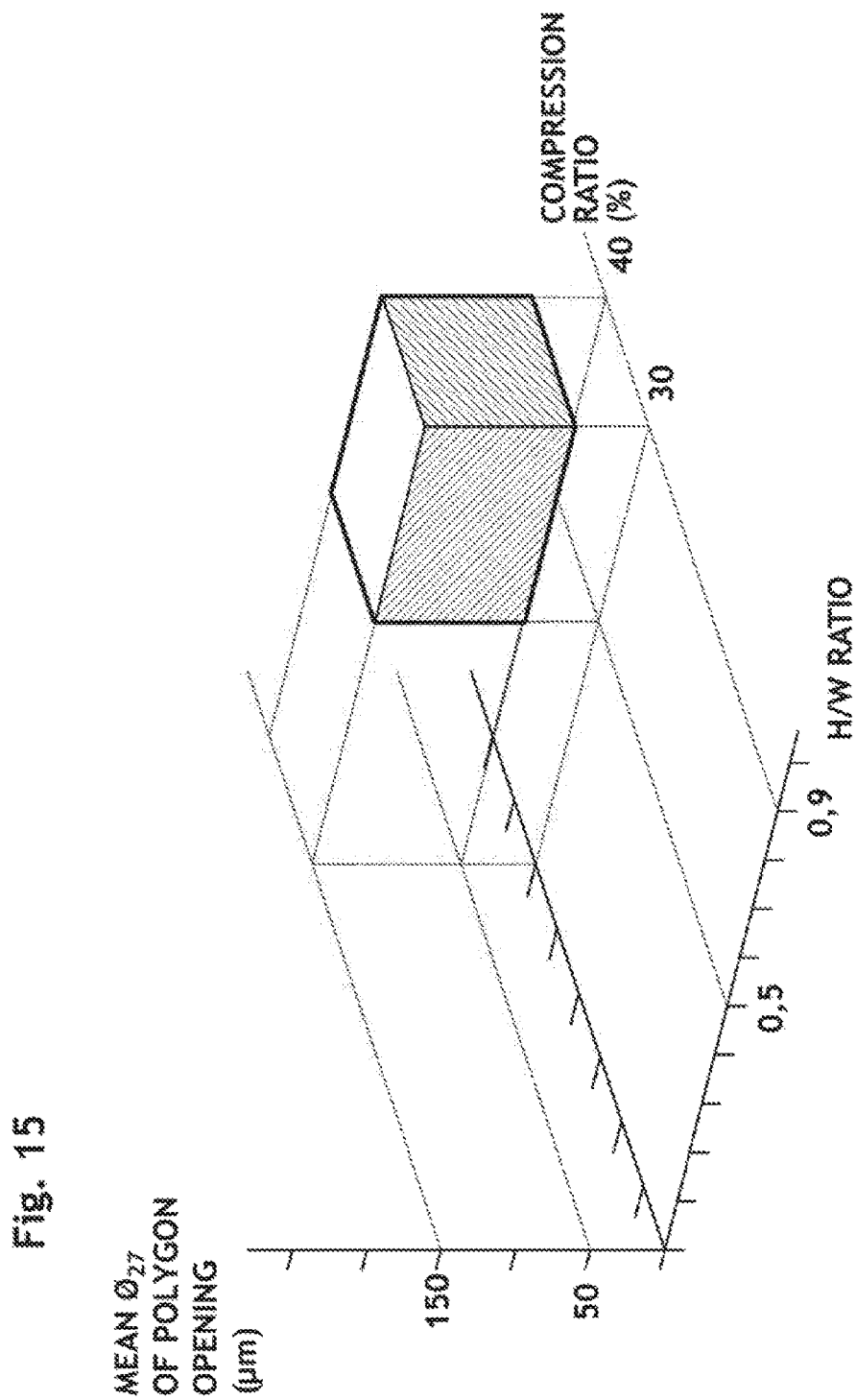

3D FILTER FOR PREVENTION OF STROKE

FIELD OF THE INVENTION

The present invention relates to implantable endoluminal prostheses and methods of using such device in preventing clots migration to avoid ischemic stroke. More particularly, the present invention is related to devices that are placed in the aorta to prevent embolic material and blood clots from entering into the branches which carry the blood to the organs, such as the brain, the kidneys or the liver.

BACKGROUND OF THE INVENTION

The aorta is the largest vessel in the body. It transports oxygenated blood from the left ventricle of the heart to every organ. The aorta extends from the heart with the aortic valve; immediately adjacent is the aortic root, followed by the ascending aorta, the aortic arch, the descending aorta, and the thoracoabdominal aorta. The abdominal section of aorta feeds the two common iliac arteries. The healthy aorta exhibits arterial compliance. That is the ability of aorta to distend and increase volume with increasing blood pressure so that the aorta yields to pressure or force without disruption. It is used as an indication of arterial stiffness.

The aortic arch is a short segment where branch vessels to the head and arms start. It has typically three branches: the brachiocephalic artery carrying the oxidized blood to the right arm, right portion of head and brain; the left carotid artery to the left head and brain; and the left subclavian artery to the left arm. There are many anomalies of the aortic arch such as the bovine arch, where there are only two branch vessels off the aortic arch. About 15% of the blood flow from the heart is supplied to the brain through these branches, and about 25% to the kidneys.

Strokes denote an abrupt impairment of brain function caused by pathologic changes occurring in blood vessels. Sudden occlusion of an artery supplying blood to the brain causes ischemic stroke. Ischemia can also occur in any organs such as the kidneys and the liver. There are two types of sources of embolic materials; the materials detached from atherosclerosis plaques of the aorta and the coagulated blood clots from the heart.

About 20% of ischemic strokes are caused by cardio-embolism. They are primarily caused by embolism of thrombotic material forming on the arterial or ventricular wall, or the left heart valves. These thrombi come away and are swept along the arterial circulation. Cardio-embolisms are generally expected when cardiac arrhythmia or structural abnormalities are present. The most common cases of cardioembolic stroke are nonrheumatic atrial fibrillation (AF), prosthetic valves, rheumatic heart disease (RHD), ischemic cardiomyopathy, congestive heart failure, myocardial infarction, post-operatory state and protruding aortic arch atheroma.

Anticoagulants are a class of drugs commonly used to prevent the blood from forming dangerous clots that could result in a stroke. Anticoagulants are frequently used in patients who are already at high-risk for stroke.

Warfarin belongs to a class of drugs called vitamin K antagonists, (VKAs) meaning that they interfere with the normal action of vitamin K, which is involved in the blood clotting process. Warfarin, the predominant anticoagulant in clinical use, reduces AF-related stroke by 64%, although this reduction is accompanied by an inherent risk of hemorrhagic complications, among which cerebral hemorrhage is especially serious. Thus up to 40% of patients with AF have the relative or absolute contraindications to anticoagulation therapy. The VKA has narrow therapeutic window and requires frequent laboratory monitoring of the international normalized ratio (INR) and subsequent dose adjustment to maintain patients within a goal INR.

The need for regular monitoring also results from the complicated pharmacokinetic profile of warfarin, the interactions with drugs, herbs, alcohol, and food, which can result in subtherapeutic (in inadequate stroke prophylaxis) or supratherapeutic (in bleeding events) drug levels. It was revealed that 44% of bleeding complications with warfarin were associated with supratherapeutic INR and that 48% of thromboembolic events occurred with subtherapeutic levels (Oake N, Fergusson D A, Forster A J, van Walraven C. Frequency of adverse events in patients with poor anticoagulation: a meta-analysis. CMAJ. 2007; 176(11):1589-94). Despite evidence-based recommendations for stroke prophylaxis with VKAs, they remain underprescribed in eligible patients with AF. Approximately 55% of patients with AF do not receive adequate stroke prophylaxis and, as result the incidence of stroke increased. Furthermore, patients who are actually treated with warfarin spend up to half of the treatment time outside the therapeutic range. This means that the full potential of warfarin to reduce stroke risk has never been fully realized nor achieved.

New oral anticoagulants (NOA) have been approved or are in development, and some are in the advanced stages of clinical research. NOAs act specifically by direct and irreversible inhibiting of the one coagulating factor. There are two classes of NOA; "direct thrombin (IIa) inhibitors" which inhibits enzyme thrombin, and "direct factor Xa inhibitors" which is central to propagation of coagulation. The NOAs have potential advantages over VKA, including a predictable anticoagulation effect that allows for fixed dosing, rapid onset and offset of action, and few drug and food interactions. In addition, they have a much wider therapeutic index compared with VKA, obviating the need for routine laboratory monitoring. However, if any bleeding occurred, the NOAs have no specific antidotes.

Prior art filter devices have not been completely successful. For example, U.S. Pat. Nos. 6,673,089 and 6,740,112 disclose a "self-expandable single-layer wire braided mesh" designed to be positioned at the bifurcation zone of the common carotid artery (CCA) to the external carotid artery (ECA). Theoretically, this braided mesh is deemed to deviate emboli to the ECA (bringing the blood in to the face) and avoid carrying it to the brain through the internal carotid artery (ICA). The rerouting efficacy of emboli into the external carotid artery (ECA) was assessed clinically by Sievert et al. in *Cardiovas Intervent Radiol* (2012) 35:406-412, "A novel carotid device for embolic diversion" in three patients during 6 to 14 months follow-ups and high risk of filter occlusion is observed in front of the ICA orifice.

As disclosed in U.S. Pat. No. 5,061,275, a braided self-expanding single-layer prosthesis has a limitation in the number of wires and diameter of wires in order to obtain a reasonable hoop force when it is deployed in a body lumen. The greater the diameter of prosthesis is, the more critical this limitation becomes. For example, if the diameter of prosthesis is 30 mm, the diameter of wire has to be between 220 and 300 µm and 36 to 64 wires otherwise the wall of prosthesis cannot exerts a sufficient hoop force against the wall of the vessel. Also, such device may need a large delivery system size which can compromise the femoral access.

U.S. Patent Application Publication No. 2003/0100940 discloses a stent-like protector device for filtering emboli originating from upstream sources and preventing them from entering the aortic arch's side branches that carry blood to the brain. Said filtering device consists of single-layer mesh-like tube in the form of a braided structure made of 100-160 filaments having 50-100 µm of diameter, the mesh opening width being 400-1000 µm. It has proven the difficulty to correctly position the devices at the aortic arch region because of its high rigidity and poor flexibility: it tends to remain in straight form while the aortic "arch" is obviously curved. Actually, in order to obtain fine mesh openings for a filtering device having a large device diameter designed for an aorta region, e.g. 25 to 45 mm, it should consist of either (i) a number of wires having small diameter, or (ii) long length of wires forming more than 150 degree of angle between braided wires.

Such configurations, however, may collapse when deployed in the aortic arch because it exhibits low hoop strength due to the low wire size as explain above. Also there is a technical limitation to braid such angulation between wires. High angulation leads to extensive foreshortening and misplacement of the device in the arch.

Furthermore, a single-layer braid with such window size (i.e., 400-1000 µm) may have a lack of capturing particles as reported by Order et al. in *J. Endovasc. Ther.* (2004) 11:211-218, particularly level of the outer side of the curve of the arch. For example, when a single-layer mesh-like tube is deployed in a curved lumen, the mesh openings at the outer side of the curve are much wider than the mesh openings in a straight configuration as shown in FIGS. 1a and 1b.

As another problem, prior art filter devices have a lack of conformability which can lead to great risk of kinking when deformed or bent to a curve matching the curvature of the aortic arch. Such kinking further complicates the placement of the device.

Accordingly, there is a need for an implantable endoluminal prosthesis being highly compliant and exhibiting an improved emboli rerouting efficacy without complications when deployed in a curved lumen such as an in aortic arch.

SUMMARY OF THE INVENTION

An object of the present invention is to provide an implantable endoluminal prosthesis suitable to be deployed within a curved vessel such as an aortic arch in front of branches supplying blood to small vessels as those which oxygen the brain, and further suitable to deflect effectively embolic material that would have flown into the aortic arch branches, into the descending aorta, thereby preventing extracranial embolus from occluding small intercranial arteries in the brain.

It is another object of the invention to provide a method for treating patients known to suffer from embolic diseases, by selectively occluding the passage of embolic material within the aortic arch and deviating it from the aortic arch branches.

It is another object of the present invention to provide an implantable filtering medical device able to provide substantially same maximal mesh opening size when deployed in a curved lumen as the one in its expanded state, thus suitable to be positioned in an aortic arch while keeping an adequate surface coverage ratio and mesh opening size at the outer side of the curve so as to obtain sufficient emboli rerouting efficacy.

It is still another object of the present invention to provide an implantable medical device and a method for improving the perfusion of organs, such as the brain, the kidneys and the liver, wherein the inlet of branch leading to said organ is covered with the implantable medical devices.

The subject of the present invention is defined in the appended independent claims. Preferred embodiment are defined in the dependent claims.

A subject of the present invention is an implantable endoluminal prosthesis consisting of a braided framework defining a cylindrical lumen and devoid of impermeable membrane. Said braided framework is self-expandable and comprises a plurality of layers of wires made of biocompatible material. Advantageously, the biocompatible material is a metallic substrate selected from the group consisting of titanium, nickel-titanium alloys such as nitinol and Nitinol-DFT®-Platinum, any type of stainless steels, or a cobalt-chromium-nickel alloys such as Phynox®. Each layer forms a mesh. The meshes form a lattice with a plurality of wires of given layers, which defines polygonal opening units when observed vertically against a wall of the implantable endoluminal prosthesis. The polygonal opening unit has preferably a quadrilateral shape, more preferably a parallelogram shape. The diameter ($Ø_{25}$) of wire is at least 30 µm and at most 220 µm, preferably at least 50 µm and at most 150 µm, more preferably at least 75 µm and at most 100 µm. The braided framework consists at least 96 and at most 512 of wires, preferably at least 128 and at most 320, more preferably at least 160, even more preferably at least 256. The ratio ($T_1/Ø_{25}$) of the thickness ($T_1$) of a wall of said implantable endoluminal prosthesis to the diameter ($Ø_{25}$) of wire is at least 2.5, preferably at least 3.0, more preferably at least 3.5, even more preferably at least 5.5, still more preferably at least 6.5, even more preferably at least 7.5. Advantageously, the meshes are interlocked so as to form a lattice with a plurality of wires of given layers, the wires being integrated in the mesh of at least one of the adjacent layers such that meshes of adjacent layers of the framework are substantially offset.

In a fully expanded state, a mean diameter ($Ø_{IC}$) of the inscribed circle (IC) of the polygonal opening units is at least 50 µm and at most 250 µm, preferably at least 75 µm at most 200 µm, more preferably at least 100 µm at most 150 µm; and the surface coverage ratio (SCR) of said braided framework (20) is more than 50% and less than 90%, preferably at least 55%, even more preferably at least 60%, still even more preferably at least 65% or greater. Advantageously, the maximal diameter of the inscribed circle is least 50 µm and at most 250 µm, preferably at least 75 µm at most 200 µm, more preferably at least 100 µm at most 150 µm in a fully expanded state.

When the implantable endoluminal prosthesis is deployed in a curved lumen having a H/W ratio between 0.5 and 0.9, a mean diameter ($Ø_{IC}$) of inscribed circle (IC) of the polygonal opening units isat least 50 µm and at most 250 µm, preferably at least 75 µm and at most 200 µm, more preferably at least 100 µm at most 150 µm. The length-related compression ratio (LCR) is between 15% and 40%, preferably between 30% and 40%. The surface coverage ratio (SCR) of the braided framework is more than 50%, preferably at least 55%, even more preferably at least 60%, still even more preferably at least 65% at the side of outer curve. Advantageously, the maximal diameter of the inscribed circle is least 50 µm and at most 250 µm, preferably at least 75 µm at most 200 µm, more preferably at least 100 µm at most 150 µm when deployed in a curved lumen having a H/W ratio between 0.5 and 0.9.

According to a preferable embodiment, the wires are made of biocompatible metal and the surface of said wires is covered with a phosphonate, preferably gem-bisphosphonate. said gem-bisphosphonate has the general formula (I), $R^3$ representing (i) —$C_{1-16}$ alkyl unsubstituted or substituted with —COOH, —OH, —$NH_2$, pyridyl, pyrrolidyl or $NR^5R^6$, (ii) —$NHR^7$, (iii) —$SR^8$ or (iv) —Cl; $R^4$ representing —H, —OH, or —Cl; $R^5$ representing —H or —$C_{1-5}$alkyl; $R^6$ representing —$C_{1-5}$alkyl; $R^7$ representing —$C_{1-10}$alkyl or —$C_{3-10}$ cycloalkyl; $R^8$ representing phenyl; at least one of $M^1$, $M^2$, $M^3$ and $M^4$ representing any metallic atom of the external surface of the wires so that at least one phosphonate moiety is covalently and directly bonded to the external surface of the wire. The bisphosphonate covers at least 50% of the external surface of the wires as monolayer and as an outermost layer. Advantageously, said gem-bisphosphonate is selected from a group consisting of etidronic acid, alendronic acid, clodronic acid, pamidronic acid, tiludronic acid, risedronic acid or a derivative thereof. As another embodiment, $R^3$ represents —$C_{1-16}$ alkyl substituted with —COOH or —OH at the terminal position and $R^4$ represents —OH.

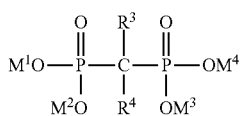

(I)

According to another preferable embodiment, said wires are coated with a phosphonate containing a hydrocarbon chain comprising 3 to 16 carbon atoms as a linier chain. The phosphorus atom of the phosphonate bonds to the hydrocarbon chain at the alpha-position. The hydrocarbon chain is further functionalized at its terminal position by a carboxylic group, a phosphonic group or a hydroxyl group. The phosphonate is covalently and directly bonded to the external surface of the wire and covers at least 50% of the external surface of the wires made of a biocompatible metal as monolayer and as an outermost layer.

Another subject of the present invention relates to the implantable endoluminal prosthesis described above for use in prevention of embolic stroke for patients suffering from atrial fibrillation, rheumatic heart disease, ischemic cardiomyopathy, congestive heart failure, myocardial infarction, post-operatory state or protruding aortic arch atheroma, or having prosthetic valves, by placing said implantable endoluminal prosthesis in front of aortic arteries which carries blood to the brain.

Still another subject of the present invention relates to the implantable endoluminal prosthesis described above for use in improving perfusion of an organ by placing said implantable endoluminal prosthesis in the aorta while covering the inlets of artery which carries blood to the organ.

BRIEF DESCRIPTION OF THE FIGURES

FIG. 1a shows a conventional single-layer braided filer device in a fully expanded state and a magnified view of a portion of the filter device.

FIG. 1b shows a conventional single-layer braided filer device deployed in a curved lumen and a magnified view of a portion of the filter device at the outer side of the curve.

FIG. 2 is a partial, cross-section view of the aorta, showing an endoluminal prosthesis according to the present invention deployed in the aortic arch.

FIG. 3 is a schematic magnified view of a portion of an (or another) endoluminal prosthesis according to the present invention.

FIGS. 4a-4c are a schematic elevation view of a portion of the endoluminal prosthesis with its first layer, the first and second layers, and the first, second and third layers, respectively, showing how to block an embolic material which is trying to go through a wall of the endoluminal prosthesis in front of an aortic branches inlet.

FIGS. 5a-5c are a schematic perspective view of the portion of the endoluminal prosthesis shown in FIGS. 4a-4c, respectively.

FIG. 6 is a side view of the endoluminal prosthesis in expanded state.

FIG. 6a is a schematic magnified view of a portion of the endoluminal prosthesis illustrated in FIG. 6.

FIG. 8 is a schematic cross-section view of the aorta showing how to measure the width and height of the aortic arch.

FIG. 10 is a perspective view of an endoluminal prosthesis according to the present invention in expanded state.

FIG. 10a is a magnified view of a portion of the endoluminal prosthesis illustrated in FIG. 10.

FIG. 11 is a perspective view of an endoluminal prosthesis according to the present invention, which is deployed in the C-curved lumen illustrated in FIG. 9.

FIG. 11a is a magnified view of a portion of the endoluminal prosthesis illustrated in FIG. 11 at the outer side of the curve.

FIG. 14 is a graph representing the relation between (x) the H/W ratio of a curved lumen where an endoluminal prosthesis according to the present invention is deployed, and (y) the mean inscribed circle diameter of mesh opening of the endoluminal prosthesis at the outer side of the curve.

FIG. 15 is a graph representing the relation among (x) the H/W ratio of a curved lumen where an endoluminal prosthesis according to the present invention is deployed, (y) the mean inscribed circle diameter of mesh opening at the outer side of the curve and (z) length-related compression ratio.

DETAILED DESCRIPTION OF THE INVENTION

Figure 7:
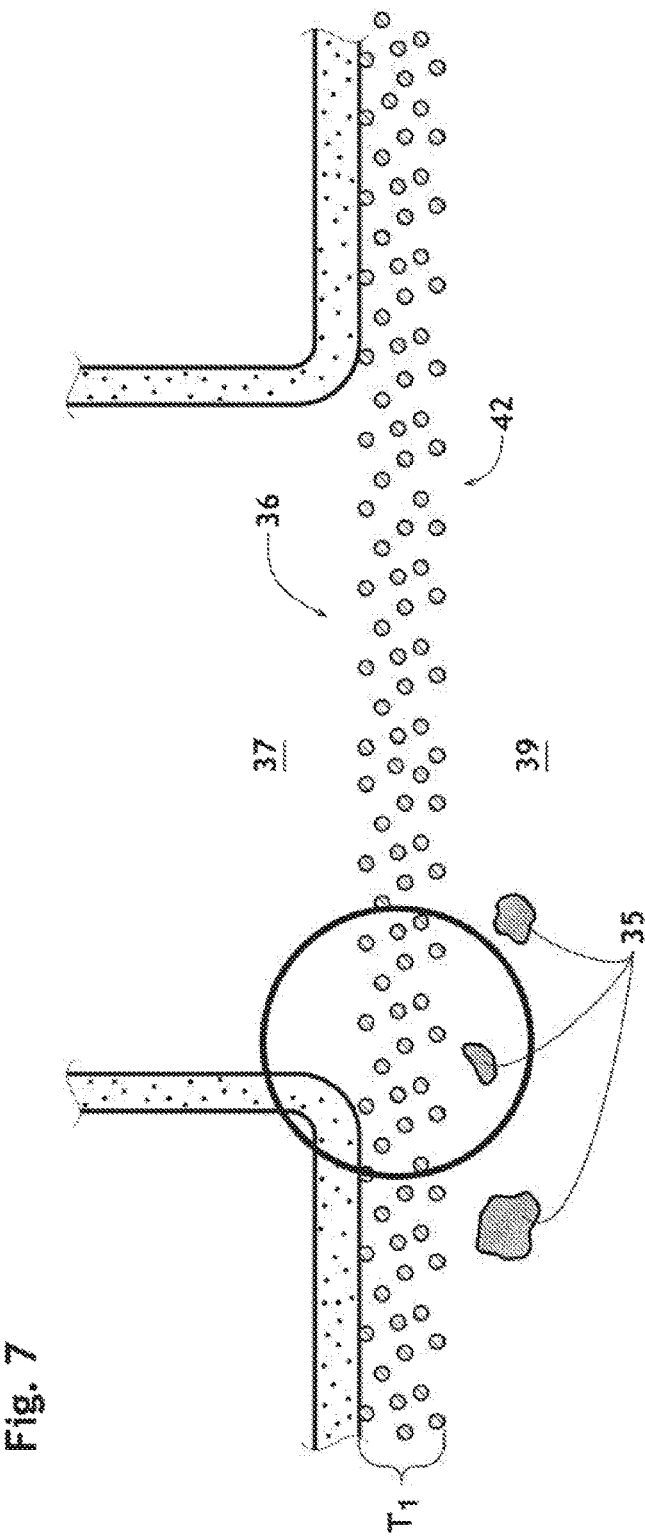
FIG. 7 is a partial, schematic magnified, cross-section view of the aortic arch at the orifice of an aortic branch, showing the deployed endoluminal prosthesis according to the present invention.

As used herein, the term "implantable" refers to an ability of a medical device to be positioned at a location within a body vessel. Implantable medical device can be configured for transient placement within a body vessel during a medical intervention (e.g., seconds, minutes, hours), or to remain in a body vessel permanently.

The terms "endoluminal" or "transluminal" prosthesis refers to a device adapted for placement in a curved or straight body vessel by procedures wherein the prosthesis is advanced within and through the lumen of a body vessel from a remote location to a target site within the body vessel. In vascular procedures, a medical device can typically be introduced "endovascularly" using a catheter over a wire guide under fluoroscopic guidance. The catheters and wire guides may be introduced through conventional access sites in the vascular system.

The term "catheter" refers to a tube that is inserted into a blood vessel to access the target site. In the present description, a "catheter" will designate either a catheter per se, or a catheter with its accessories, meaning needle, guide wire, introducer sheath and other common suitable medical devices known by the man skilled in the art.

The term "preventing" includes rejecting or inhibiting the embolic material from entering a specified blood vessel, such as a branch blood vessel.

To avoid any confusion, in the description herein below, the terms of "opening", "pore" and "window" have their ordinary meaning and are also used interchangeably to refer to a open channel or passageway from one face or surface of a medical device to its other face or surface. Similarly, the terms of "inlet", "junction" and "orifice" refer to an area in vasculature where at least one branch blood vessel diverges the main blood vessel.

The term "endothelialisation" refers to a cellular process resulting in ingrowth of the endothelial cells onto a device.

The term "permanent" refers to a medical device which may be placed in a blood vessel and will remain in the blood vessel for a long period of time (e.g. months, years) and possibly for the remainder of the patient's life.

The terms "embolus", "embolic material" and "filtrate" refer to a clot or other biologic material which has been brought to its site of lodgement by the blood flow. The obstructing material is most often a blood clot (i.e., thrombus), but may be a fat globule (due to atherosclerosis), piece of tissue or clump of bacteria.

An implantable endoluminal prosthesis 1 according to the present invention consists of a braided framework 20 which defines a cylindrical lumen 21. The device is devoid of impermeable membrane. The braided framework 20 is configured to take a compressed shape having a relatively small and relatively uniform diameter when disposed within a delivery system (i.e., "in compressed state"), and to take spontaneously a deployed shape having radially expanded diameter within the delivered location such as a body lumen (i.e., "in deployed state") as shown in FIGS. 2 and 11. As used herein the term of "expanded shape" or "expanded state" refers to respectively a shape or state resulting from the self-expanding properties of a self-spring-back object (e.g., braided framework 20) when it is expanded without any outer compression force (i.e., non-constricted state) as shown in FIG. 10. Beside these definitions, the term "nominal diameter" designates the diameter of the stent-filter when placed in the targeted a vessel. Generally, the nominal diameter ($\varnothing_{nor}$) of a self-expandable device designed to be placed permanently inside a body lumen is 10 to 25% smaller than the external diameter of said device when deployed without external compression force ($\varnothing_{exp}$). Since a diameter ($\varnothing_{39}$) of aorta 39 is generally between 20 mm and 40 mm, the endoluminal prosthesis 1 according to the present invention is accordingly designed and/or manufactured to have a diameter ($\varnothing_{1\_exp}$) between 22 mm and 50 mm in expanded state. Variations of the diameter of the prosthesis influence, in turn, its length. The length ($L_{1\_dep}$) of the endoluminal prosthesis 1 according to the invention in deployed state is thus greater than its length ($L_{1\_exp}$) in expanded state. The length-related compression ratio (LCR) of the prosthesis 1 can be defined by the relation:

$$LCR = (L_{1\_dep} - L_{1\_exp})/L_{1\_exp}$$

Figure 9:
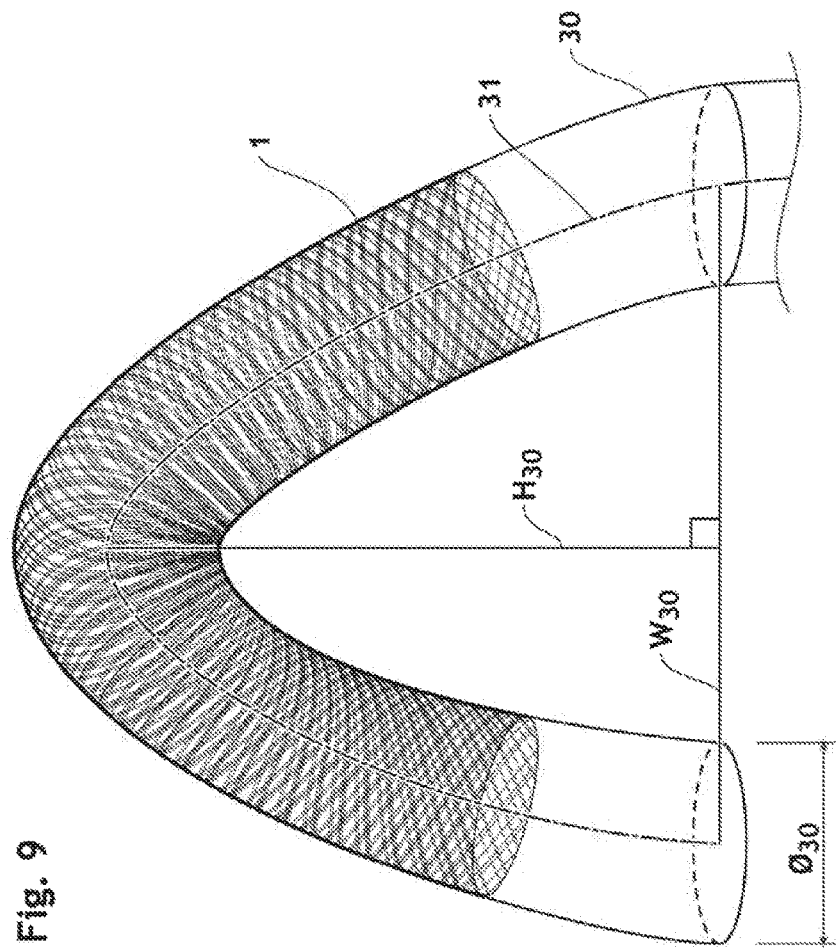
FIG. 9 is a perspective view of a C-curved lumen, showing an endoluminal prosthesis deployed therein.

When the endoluminal prosthesis 1 is deployed in a curved lumen 30 as shown in FIG. 9, its length ($L_{1\_dep}$) in deployed state is measured along the midpoint 31 of the curve as indicated in FIG. 11.

The curve of the aortic arch 39 is generally defined by measuring the width ($W_{39}$) and height ($H_{39}$) of the curve as described by Ou et al. in *J. Thrac. Cardiovasc. Surg.* 2006; 132: 1105-1111. Width ($W_{39}$) is measured as the maximal horizontal distance between the midpoints 31 of the ascending and descending aorta 39 close to the axial plane going through the right pulmonary artery (RPA); and height ($H_{39}$) of the aortic arch is measured maximal vertical distance between ($W_{39}$) and the highest midpoint 31 of the aortic arch 39 as depicted in FIG. 8. The ratio $H_{39}/W_{39}$ is generally in a range of 0.5 and 0.9. For example, when the value is 0.9, the aortic arch is extremely acute as depicted, as the worst scenario, in FIG. 9. This can cause a kinking of conventional filters, as described previously, which have poor hoop force and also make the difference of mesh opening between its straight form and its deployed one greater in comparison with the one deployed in a curve having about 0.6 of the H/W ratio which is usually observed in healthy aorta. One of the endoluminal prosthesis advantages according to the present invention is that the mesh windows are not compromised by this extremely acute curve because of the combination of the layers.

The braided framework 20 comprises a plurality of layers 22, 23, 24 of wires 25 made of biocompatible material. The wires have a diameter ($\varnothing_{25}$) of at least 30 µm and at most 220 µm, preferably at least 50 µm and at most 150 µm, more preferably at least 75 µm and at most 100 µm. Each layer of the braided framework 20 forms a mesh. When observed normal with respect to a wall of the implantable endoluminal prosthesis 1, meshes of the braided frame 20 form a lattices with a plurality of level of wires 25. Preferably, the meshes are interlocked to each other so as to form an interlocked multi-layer structure. The term "interlocked multi-layer" refers to a framework comprising multiple layers, 22, 23, 24, whose plies are not distinct at the time of braiding, for example a given number of wires of the plies 22a of the first layer 22 being interlocked with the plies 23a of the second layer 23 and/or other layers 24. Said interlocked multi-layer, for example, can be formed by using the braiding machine described in EP1248372. The braided framework 20 of the endoluminal prosthesis 1 is made of at least 96 and at most 512 of wires 25, preferably more than at least 128 and at most 320, more preferably more than at least 160, even more preferably at least 256.

The lattice defines opening units 26 having a polygonal shape defined by sides (i.e. wire segments). The polygonal shape is preferably quadrangle, more preferably parallelogram. "Parallelogram" means a simple quadrilateral with two pairs of parallel sides; the facing sides of a parallelogram are of equal length; the opposite angles of a parallelogram are of equal measure; and the diagonals bisect each other. Parallelograms include squares, rectangles, and lozenges. As used herein, "inscribed circle" 27 refers to the largest circle that can be drawn inside the polygonal opening unit 26 and tangent to a maximum of its sides (i.e. wires segments 25) as depicted in FIGS. 1a, 1b, 3, 10a and 11a.

The size of inscribed circle 27 directly reflects the efficacy to deflect embolic material 35, particularly microembolus that would have flown into the aortic branches, to the descending aorta. "Microembolus" refers to an embolus of microscopic size, for example, a tiny blood clot or a little clump of bacteria. Micro-emboli are either gaseous or solid embolic material. The gaseous micro-emboli can originate from mechanically induced cavitation created by a prosthetic heart valve. They have an approximate diameter of 4 µm and cause normally no deleterious effect on the brain. In contrast solid microemboli are much bigger than gaseous micorembuli, having an approximate diameter of 100 µm. The larger size of solid microemboli compared to the size of capillaries (diameter 7-10 µm) can cause blockage of micro circulation. In J. Endovasc. Ther, 2009; 16; 161-167, "Reduction of cerebral embolixation in carotid angioplasty: An in-vitro experiment comparing 2 cerebral protection devices" published by Charalambous et. al., either gaseous or small emboli having diameter less than 200 µm cause only clinically unperceived cerebral ischemia.

Therefore, in order to reroute embolic material having more than 200 µm, a mean diameter ($\varnothing_{27}$) of inscribed circle 27 (IC) of polygonal openings 26 is preferably at most 200 µm in a curved deployed configuration to comply to the aortic arch geometry, preferably at most 150 µm, more preferably at most 100 µm. At the same time, since the openings should be large enough to let the blood components get through the wall of the prosthesis 1 and keep adequate perfusion, the mean IC should be at least 50 µm, preferably at least 75 µm. The mean diameter ($\varnothing_{27}$) of inscribed circle 27 (IC) of polygonal openings 26 means the value found by addint together all the diameters of inscribed circle 27 and dividing the total by the total number of openings 26.

One of advantages of the implantable endoluminal prosthesis according to the present invention is that the prosthesis 1, having higher value of $T_1/\varnothing_{25}$, can prevent effectively an embolic material 35 from going through its wall as shown in FIGS. 4a-4c, 5a-5c and 6a in comparison with a conventional filter having less than 2.0 of $T_1/\varnothing_{25}$. The ratio ($T_1/\varnothing_{25}$) of the wall thickness ($T_1$) of the endoluminal prosthesis to the wire diameter ($\varnothing_{25}$) being at least 2.0 characterizes a braided framework having more than a single layer of mesh. The greater the ratio $T_1/\varnothing_{25}$, the more layers the braided framework 20 will comprise. Each wire forming multiple-layers aligned substantially parallel in the wall, as shown in FIG. 6, has a chance to deviate or block an embolic material trying to get through the wall of the endoluminal prosthesis 1 as schematically explained in FIGS. 4a-4c and 5a-5c, the present structure can thus increase the emboli rerouting efficacy.

Figure 12:
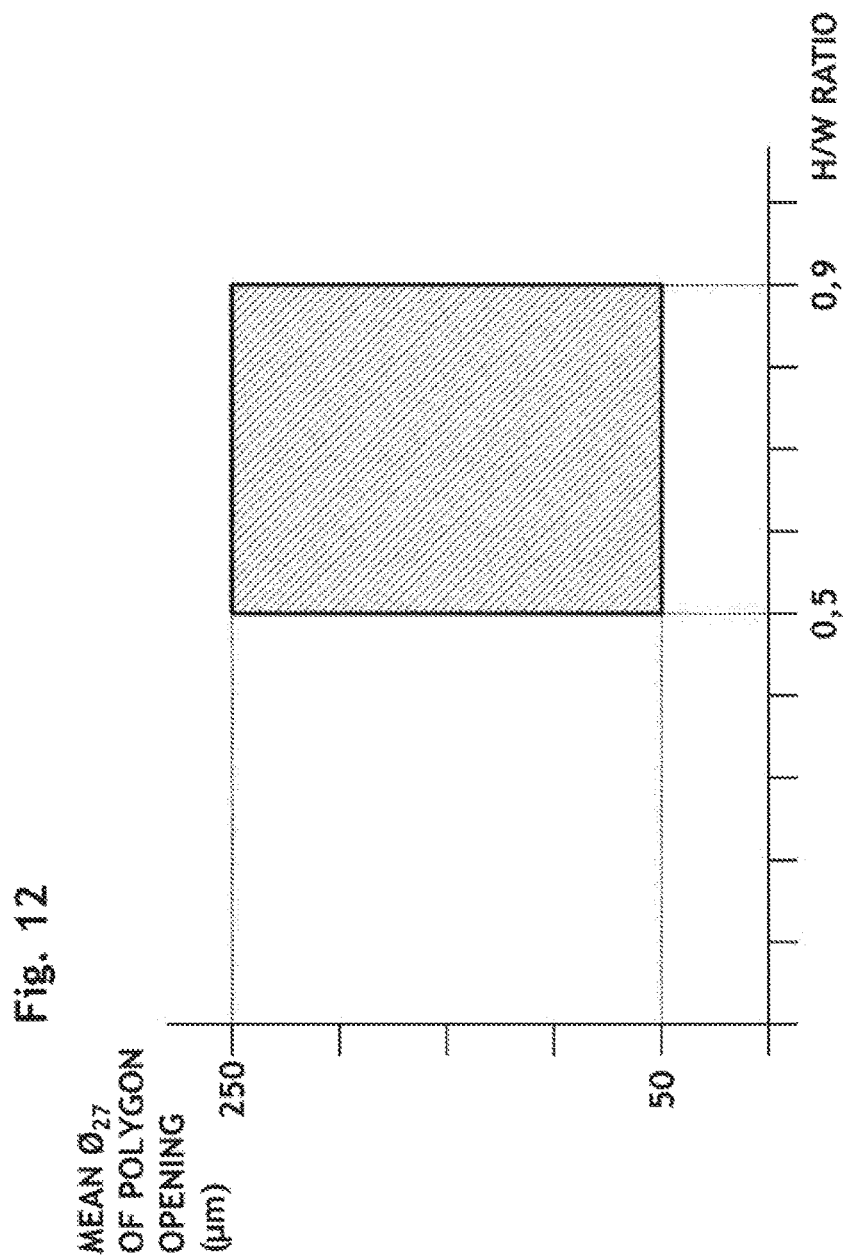
FIG. 12 is a graph representing the relation between (x) the H/W ratio of a curved lumen where an endoluminal prosthesis according to the present invention is deployed, and (y) the mean inscribed circle diameter of mesh opening of the endoluminal prosthesis at the outer side of the curve.

Furthermore, interlocked multiple-layer configuration having more than 2.5 of $T_1/\varnothing_{25}$ provides an important technical property: when it is deployed in a curved lumen having the H/W ratio between 0.5 and 0.9, the mean inscribed circle diameter ($\varnothing_{27}$) of opening units is at least 50 µm and at most 250 µm, preferably at least 75 µm and at most 200 µm, more preferably at least 100 µm and at most 150 µm at the outer side of the curve 29 as defined in FIGS. 12 and 14, respectively. Since the orifices of the aortic branches are located at the outer side of the arch, it is most important to set an optimal opening size at the outer side when deployed in an aortic arch geometry in order to improve filtering efficacy. Wires of the interlocked multiple-layer configuration according to the present invention shift to have a regular distance between adjacent parallel wires in a curved, deployed state, resulting in that the mean inscribe diameter ($\varnothing_{27}$) stays almost the same as the one in straight configuration of its expanded state as shown in FIGS. 10a and 11a.

Figure 13:
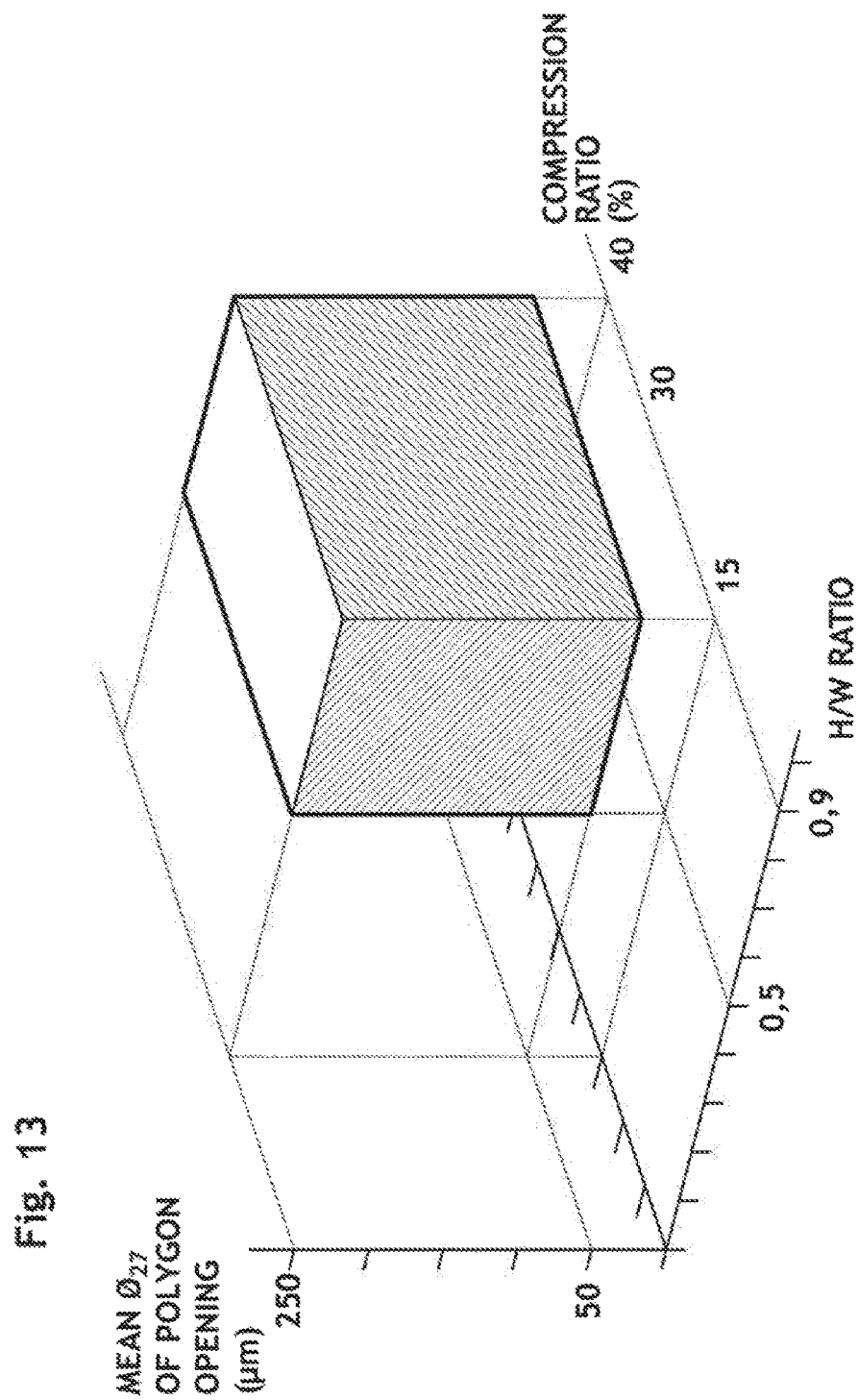
FIG. 13 is a graph representing the relation among (x) the H/W ratio of a curved lumen where an endoluminal prosthesis according to the present invention is deployed, (y) the mean inscribed circle diameter of mesh opening at the outer side of the curve and (z) length-related compression ratio.

As mentioned above, the aorta exhibits arterial compliance. An endoluminal prosthesis for aorta should have enough hoop force to deal with the arterial compliance; otherwise it may cause complications such as device migration and kinking. The device migration is an undesired displacement of the device after implantation and kinking is a phenomenon well known to men skilled in the art to occur during stent placement in a curved vessel. In order to obtain sufficient hoop force, the length-related compression ratio (LCR) also should be in a range of 15% and 40%, preferably 30% and 40%. The relations of LCR to the H/W ratio and the mean inscribed circle diameter according to the present invention are shown in FIGS. 13 and 15.

The surface coverage ratio (SCR) of the braided framework 20 is defined by the relation:

$$SCR = S_w/S_t$$

wherein: "$S_w$" is the actual surface covered by wires 25 composing the braided framework 20, and "$S_t$" is the total surface area of the wall of the braided framework 20. In a fully expanded state, SCR of the endoluminal prosthesis 1 is more than 50%, preferably at least 55%, even more preferably at least 60%, still even more preferably at least 65%. When deployed in a C-curved lumen 30 having a nominal diameter of the endoluminal prosthesis 1 and the $H_{30}/W_{30}$ ratio between 0.5 and 0.9, the braided framework 20 with at least 3.5 of the ratio of $T_1/\varnothing_{25}$ (preferably 5.5, more preferably at least 6.5, even more preferably at least 7.5) can provide almost same surface coverage ratio (SCR) along its outer curve 29 as the one in its straight configuration, i.e. more than 50%. It is another advantage of the present invention, resulting in improvement of emboli rerouting efficacy.

Filtering devices known in the art often become clogged and need to be cleaned or even replaced. An endoluminal prosthesis designed to be positioned permanently in a blood vessel should have an inherent ability to clean itself or be cleaned by endogenous forces or effect so as to avoid periodic cleaning by a physician or removal of the device from the blood vessel.

Figure 7B:
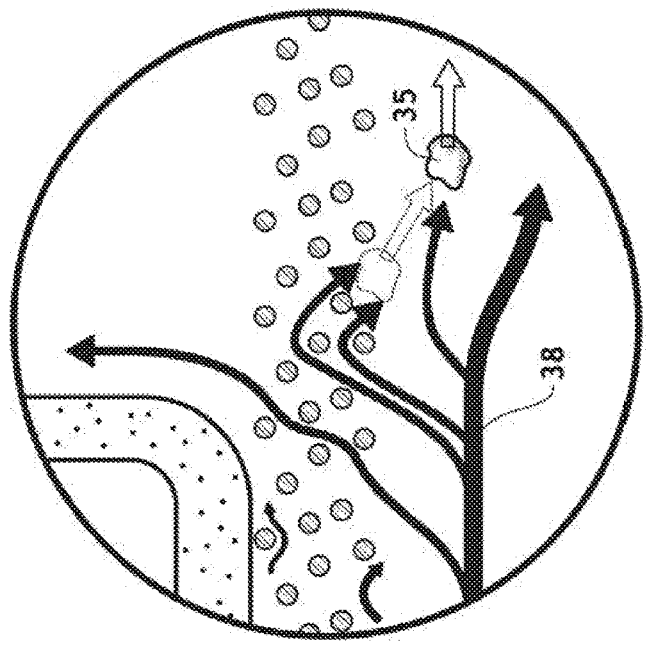
FIGS. 7a and 7b are a schematic magnified view illustrated in FIG. 7, showing how to an embolic material temporally located in front of an aortic orifice is flushed away during the cardiac cycle.
Figure 7A:
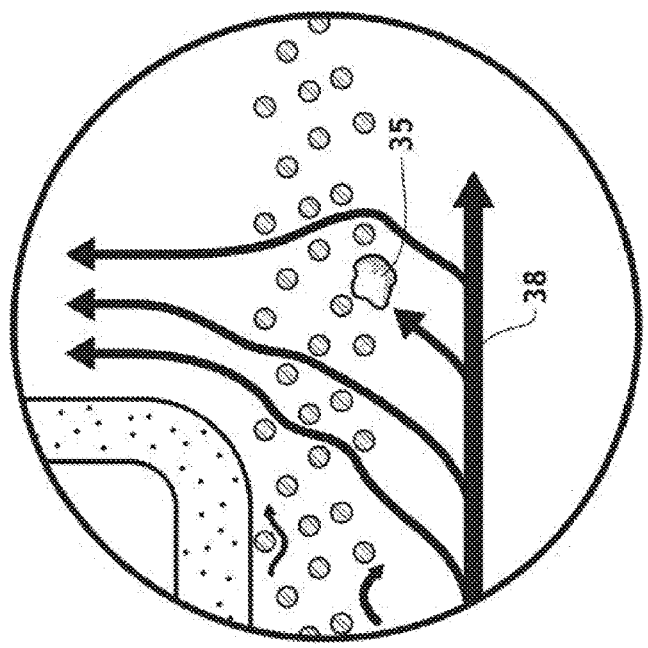

The endoluminal prosthesis 1 having a sufficient wall thickness ($T_1$) against the size of the opening 26, i.e. the inscribed circle diameter ($\varnothing_{27}$), imparts high self-cleaning property in comparison with conventional filter devices. As shown in FIGS. 7, 7a and 7b, some embolic materials 35 flowing about an orifice 36 of aortic branch 37 are temporally pushed against an interior surface 42 of the implantable endoluminal prosthesis 1 in front of the aortic branches 37 as a result of blood inflow through a wall thereof during the ventricular systole and the relaxation phase of the cardiac cycle. Thanks to the sufficient wall thickness $T_1$ of the braided framework 26, these embolic materials 35 are kept trapped on the interior surface 42 instead of passing through the wall, and are then flushed away and back into the aortic blood stream 38 during the atria systole, as a result of the flushing expelling force. The term "flushing expelling force" refers to an inherent property of the implantable endoluminal prosthesis. Specifically, it is the force that is imparted on the embolic material 35 by the flowing aortic blood 38 with which it comes in contact.

Studies and experiments carried by the inventor led to surprising and unexpected conclusions. If the ratio $T_1/\varnothing_{25}$ is smaller than 2.0 as in conventional filters, the embolic material 35 is either flushed through the mesh openings and enters into the arterial branches or accumulates till it blocks the blood flow at the orifice of the branches. The greater the ratio $T_1/\emptyset_{25}$, the greater the flushing expel force the endoluminal prosthesis 1 will exhibit.

Therefore, the present endoluminal prosthesis 1 reduces the occlusion risk of the branches orifice covered thereby, resulting in an increase of safety in use. The ratio $T_1/\emptyset_{25}$ should be at least 2.5, preferably at least 3.0, more preferably 3.5, even more preferably 5.5, still more preferably at least 6.5, even more preferably at least 7.5, so as to improve safety of the device.

The biocompatible material preferably metallic substrate selected from a group consisting of stainless steels (e.g., 316, 316L or 304); nickel-titanium alloys including shape memory or superelastic types (e.g., nitinol, Nitinol-DFT®-Platinum); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; magnesium alloys; titanium alloys (e.g., TiC, TiN); tantalum alloys (e.g., TaC, TaN); L605. Said metallic substrate is preferably selected from the group consisting of titanium, nickel-titanium alloys such as nitinol and Nitinol-DFT®-Platinum, any type of stainless steels, or a cobalt-chromium-nickel alloys such as Phynox®.

As additional surprising effect, the perfusion in the branches is improved in accordance with the increase of $T_1/\emptyset_{25}$ value. "Perfusion" is, in physiology, the process of a body delivering blood to capillary bed in its biological tissue. The terms "hypoperfusion" and "hyperperfusion" measure the perfusion level relative to a tissue's current need to meet its metabolic needs. Since the implantable medical device according to the present invention increases the perfusion in the aortic branches covered thereby, the function of organs to which the aortic branches carries the blood is improved.

As indicated in US Patent Application No. US2006/0015138, it is known that preferred coating for a filter means should be highly hydrophobic such as polytetraethylfluorine (PTFE), polyvinylfluoridene (PVDF), and polyalilene so as to decrease the degree of friction between the blood and the surface of the device and enhance the blood inflow to branches.

Surprisingly, by combining with the above-mentioned structure of braided framework 20, a coating of a phosphorous-based acid formed on the endoluminal prosthesis 1 can provide improved embolic rerouting efficacy while keeping an adequate permeability of the braided framework 20 at portions on orifices of aortic branches. The phosphorous-based acid used can be selected from organic phosphonic acids having the formula $H_2R^1PO_3$ wherein $R^1$ is an organic ligand with a carbon atom directly bonded to phosphorus at its alpha-position. At least one phosphonate moiety of the phosphonate is covalently and directly bonded to the external surface of the metallic substrate in the coating.

In one preferred embodiment, said organic ligand comprises a hydrocarbon chain with between 3 and 16 carbon atoms. The organic ligand is further functionalized at its terminal carbon (i.e. at the opposite end of the alpha-position) so as to increase an interaction between the coating and the embolic material 35 flowing in an aorta. Said functional groups may be a hydroxyl group, a carboxylic group, an amino group, a thiol group, phosphonic group or chemical derivatives thereof. Preferably, the substituent is a carboxylic group, phosphonic group or hydroxyl groups.

Said coatings provide improved embolic rerouting efficacy while promoting endothelium formation on the interior wall of the implantable medical device covering the artery wall except portions covering branches' orifices, and keeping an adequate permeability of the braided framework at portions in front of aortic branches.

Preferably, the number of carbon atoms comprised in the organic ligand is at least 6 and at most 16 as a linier chain, more preferably at least 8 and at most 12. Said phosphonic acid may be selected from a group consisting of 6-phosphonohexanoic acid, 11-phosphonoundecanoic acid, 16-phosphonohexadecanoic acid, 1,8-octanediphosphonic acid, 1,10-decyldiphosphonic acid and (12-phosphonododecyl)phosphonic acid. One of carbon atoms, —(CH$_2$)—, of the organic ligand may be substituted by a tertiary amino group, —N(R$^2$Y)—. The substituent of tertiary amino group has an alkyl group, —R$^2$Y, the terminal carbon of which is functionalized by carboxylic acid, phosphonic acid or a derivative thereof. Said phosphonic acid comprising the tertiary amino group is preferably selected from a group consisting of N-(phosphonomethyl)iminodiacetic acid and N,N-bis(phosphonomethyl) glycine). In another preferred embodiment, the phosphonic acid may be further functionalized at the alpha-position of the organic ligand by a supplementary phosphonic acid and/or hydroxyl group such as 5-hydroxy-5,5'-bis(phosphono)pentanoic acid. In another preferred embodiment, coatings are formed from germinal bisphosphonates characterized by two C—P bonds located on the same carbon atom defining a P—C—P structure. Said gem-bisphosphonate groups has the general formula (I),

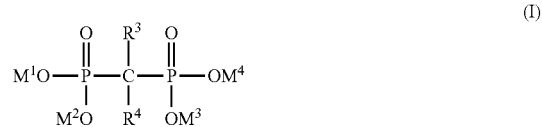

(I)

$R^3$ representing (i) —C$_{1-16}$ alkyl unsubstituted or substituted with —COOH, —OH, —NH$_2$, pyridyl, pyrrolidyl or NR$^5$R$^6$; (ii) —NHR$^7$; (iii) —SR$^8$; or (iv) —Cl; R$^4$ representing —H, —OH, or —Cl; R$^5$ representing —H or —C$_{1-5}$ alkyl; R$^6$ representing —C$_{1-5}$ alkyl; R$^7$ representing —C$_{1-10}$ alkyl or —C$_{3-10}$ cycloalkyl; R$^8$ representing phenyl. At least one of M$^1$, M$^2$, M$^3$ and M$^4$ represents any metallic atom in the external surface of the implantable medical device. It means that at least one phosphonate moiety of the bisphosphonate is covalently and directly bonded to the external surface of the metallic substrate in the coating. The bisphosphonate covers at least 50% of the external surface of the metallic substrate as monolayer and as an outermost layer. Preferably R$^3$ represents —C$_{1-16}$alkyl substituted with —COOH or —OH at the terminal position; and R$^4$ represents —OH. Preferably, said gem-bisphosphonate is etidronic acid, alendronic acid, clodronic acid, pamidronic acid, tiludronic acid, risedronic acid or a derivative thereof.

Method of Deployment

According to one preferred embodiment, the endoluminal prosthesis 1 according to the present invention is deployed by using an endoluminal prosthesis delivery apparatus. This apparatus is designed to be driven by an operator from the proximal site on through the vascular system so that the distal end of the apparatus can be brought close to the implantation site, where the prosthesis 1 can be unloaded from the distal end of the apparatus. The delivery apparatus comprises the prosthesis 1, a prosthesis receiving region wherein the prosthesis has been introduced, a central inner shaft and a retracting sheath. Preferably, the apparatus further comprises a self-expanding holding means that is compressed within the sheath, the distal portion of which encircles the proximal potion of the prosthesis, and the proximal end of which is permanently joined to the inner shaft with a joint so as to provide the apparatus with a function of re-sheathing a partially unsheathed prosthesis into a retracting sheath. To deploy the prosthesis 1 at a desired location in the aorta, the distal end of the retracting sheath is brought to the location and the retracting sheath is progressively withdrawn from over the prosthesis 1 toward the proximal end of the delivery apparatus. Once the sheath is adjacent the proximal end of the holding means, the prosthesis 1 is partially allowed to self-expand to a deployed shape. By continually retracting the sheath proximally, the holding means is released from the sheath and deploys while under the effect of the temperature of the organism and/or because of their inherent elasticity. In order to prevent a prosthesis migration after implantation, an oversized prosthesis 1 is generally chosen which has a diameter in its "nominal" expanded state being 10-40% greater than the diameter of the body lumen at the implantation site. Such prosthesis 1 exerts a sufficient radial force on an inner wall of the body lumen and is thus fixed firmly where it is implanted. Since, upon deployment, the radial force provided by the deployed part of the prosthesis 1 onto the wall of the aorta becomes greater than the grasping force of the deployed holding means in its deployed state, the holding means can release the prosthesis at the deployed position without undesired longitudinal displacement when retracting the inner shaft proximally together with the sheath.

The invention claimed is:

1. An implantable endoluminal prosthesis comprising: a braided framework defining a cylindrical lumen devoid of impermeable membrane, said braided framework being self-expandable, comprising a plurality of layers of wires made of biocompatible material, each layer forming a mesh, the meshes forming a lattice with a plurality of wires of given layers, the lattice defining polygonal opening units when observed normal to a wall of the implantable endoluminal prosthesis, a diameter ($\phi_{25}$) of the wires being at least 30 μm and at most 150 μm, a mean diameter ($\phi_{27}$) of an inscribed circle of the polygonal opening units being at least 75 μm and at most 200 μm in a fully expanded state, characterized in that:
the braided framework consists of at least 128 and at most 512 wires;
a ratio ($T_1\phi_{25}$) of a thickness ($T_1$) of a wall of said implantable endoluminal prosthesis to the diameter ($\phi_{25}$) of wire is at least 3.0;
in the fully expanded state, a surface coverage ratio (SCR) of said braided framework is more than 50% and less than 90%;
when the implantable endoluminal prosthesis is deployed in a curved lumen having a H/W ratio between 0.5 and 0.9, the mean diameter ($\phi_{27}$) of the inscribed circle of opening units is at least 75 μm and at most 200 μm, a length-related compression ratio (LCR) being between 15% and 40%, and the surface coverage ratio (SCR) of the braided framework being more than 50% at a side of outer curve.

2. The implantable endoluminal prosthesis according to claim 1, wherein the meshes are interlocked forming the lattice with the plurality of wires of given layers, the wires being integrated in the mesh of at least one of the adjacent layers such that meshes of adjacent layers of the framework are substantially offset.

3. The implantable endoluminal prosthesis according to claim 2, wherein the ratio ($T_1/\phi_{25}$) is at least 3.5.

4. The implantable endoluminal prosthesis according to claim 3, wherein the braided framework is at least 256 wires to 512 wires.

5. The implantable endoluminal prosthesis according to claim 4, wherein the wires are made of biocompatible metal, a surface of said wires being covered with a gem-bisphosphonate, said gem-bisphosphonate groups having the general formula (I),

$R^3$ representing: (i) —$C_{1-16}$ alkyl unsubstituted or substituted with —COOH, —OH, —$NH_2$, pyridyl, pyrrolidyl or $NR^5R^6$; (ii) —$NHR^7$; (iii) —$SR8$; or (iv) —Cl;
$R^4$ representing —H, —OH, or —Cl;
$R^5$ representing —H or —$C_{1-5}$ alkyl;
$R^6$ representing —$C_{1-5}$ alkyl;
$R^7$ representing —$C_{1-10}$ alkyl or —$C_{3-10}$cycloalkyl;
$R^8$ representing phenyl;
at least one of $M^1$, $M^2$, $M^3$ and $M^4$ representing any metallic atom of the external surface of the wire, so that at least one phosphonate moiety is covalently and directly bonded to the external surface of the wire, and the bisphosphonate covering at least 50% of the external surface of the wires as monolayer and as an outermost layer.

6. The implantable endoluminal prosthesis according to claim 5, wherein said gem-bisphosphonate is etidronic acid, alendronic acid, clodronic acid, pamidronic acid, tiludronic acid, risedronic acid or a derivative thereof.

7. The implantable endoluminal prosthesis according to claim 4, wherein said wires are coated with phosphonate containing a hydrocarbon chain comprising 3 to 16 carbon atoms as a linear chain, the phosphorus atom of the phosphonate bonding to the hydrocarbon chain at the alpha-position, said hydrocarbon chain being further functionalized at its terminal position by a carboxylic group, a phosphonic group or a hydroxyl group, and at least one of $M^1$ and $M^2$ representing any metallic atom of an external surface of an implantable medical device, the phosphonate being covalently and directly bonded to the external surface of the wire and covering at least 50% of the external surface of the implantable medical device as monolayer and as an outermost layer.

8. The implantable endoluminal prosthesis according to claim 4, wherein the biocompatible material is a metallic substrate selected from the group consisting of titanium, nickel-titanium alloys, any type of stainless steels, or a cobalt-chromium-nickel alloys.

9. The implantable endoluminal prosthesis according claim 1, wherein the surface coverage ratio (SCR) of said braided framework is at least 55% to 90% in a fully expanded state.

10. The implantable endoluminal prosthesis according to claim 1, wherein when an implantable medical device is deployed in a curved lumen having H/W ratio between 0.5 and 0.9, the mean diameter ($\phi_{27}$) of inscribed circle of opening units is at least 100 µm and at most 150 µm, the length-related compression ratio (LCR) being between 30% and 40% at the outer side of the curve.

11. The implantable endoluminal prosthesis according to claim 10, wherein the surface coverage ratio (SCR) of the braided framework is at least 55% to 90% at the outer side of the curve.

12. The implantable endoluminal prosthesis according to claim 1, wherein the diameter ($\phi_{25}$) of the wires is at least 50 µm to 150 µm.

13. The implantable endoluminal prosthesis according to claim 1, wherein the mean diameter ($\phi_{27}$) of the inscribed circle of the polygonal opening units is at least 100 µm and at most 150 µm in fully expanded state.

14. A method for prevention of embolic stroke for patients suffering from atrial fibrillation, rheumatic heart disease, ischemic cardiomyopathy, congestive heart failure, myocardial infarction, post-operatory state or protruding aortic arch atheroma, or having prosthetic valves comprising placing said implantable endoluminal prosthesis of claim 1 in front of aortic arteries which carry blood to the brain.

15. A method for improving perfusion of an organ comprising: placing said implantable endoluminal prosthesis of claim 1 in the aorta while covering the inlets of arteries which carry blood to the organ.

* * * * *